United States Patent [19]

Seybert

[11] 4,153,680
[45] May 8, 1979

[54] HYDROUS SILICA GEL CONTAINING DENTIFRICE

[75] Inventor: Earl K. Seybert, Towson, Md.

[73] Assignee: W. R. Grace & Co., New York, N.Y.

[21] Appl. No.: 852,758

[22] Filed: Nov. 18, 1977

Related U.S. Application Data

[63] Continuation of Ser. No. 655,601, Feb. 5, 1976, abandoned.

[51] Int. Cl.² ............................................. A61K 7/16
[52] U.S. Cl. ................................................... 424/49
[58] Field of Search .................................. 424/49–58; 252/317; 423/339

[56] References Cited

U.S. PATENT DOCUMENTS

| | | | |
|---|---|---|---|
| 2,731,326 | 1/1956 | Alexander et al. | 23/182 |
| 3,004,921 | 10/1961 | Stossel | 252/309 |
| 3,538,230 | 11/1970 | Pader et al. | 424/50 |
| 3,689,637 | 9/1972 | Pader | 424/52 |
| 3,716,493 | 2/1973 | Acker et al. | 252/317 |
| 3,803,301 | 4/1974 | Cordon et al. | 424/49 |
| 3,864,470 | 2/1975 | Watson | 424/49 |
| 3,893,840 | 7/1975 | Wason | 106/288 B |
| 3,928,541 | 12/1975 | Wason | 423/339 |
| 3,934,000 | 1/1976 | Barth | 424/49 |
| 3,935,306 | 1/1976 | Roberts et al. | 424/49 |

*Primary Examiner*—Shep K. Rose
*Attorney, Agent, or Firm*—Mark T. Collins

[57] ABSTRACT

This invention relates to polishing agents for use in dentifrice formulations. More particularly, this invention relates to the use of silica gels having a water content of 15 to 35 percent as polishing agents in dentifrice formulations.

9 Claims, No Drawings

HYDROUS SILICA GEL CONTAINING DENTIFRICE

This is a continuation of application Ser. No. 655,601 filed Feb. 5, 1976, now abandoned.

Various types of silica have been used in dentifrice formulations. These include silica aerogels, silica xerogels, silica hydrogels and pyrogenic silicas. Generally, the silica aerogel or pyrogenic silica is added as a thickening or bodying agent and accounts for very little of the polishing characteristics of the formulation. These are poor polishing agents since the particle aggregates, which are in the 1 to 20 micron range, are very fragile and readily break down to an average particle size of less than 1 micron. At particle sizes of less than 1 micron, the polishing action of a silica is very low. The only types of silica which have been known as good polishing agents up to this time are silica xerogels. A silica xerogel is a silica which has had its structure considerably shrunken during drying. Silica hydrogels are not good polishing materials since, due to their high porosity, they are quite fragile and rapidly decrepitate when subjected to the forces of a brush.

In regard to this degree of shrinking of a silica to produce a silica xerogel, it should be considered that an acid set silica hydrogel has a water content of about 75 percent by weight, with 25 percent by weight being silica. If no shrinkage occurred during drying, a silica would have about a 4 cc/g pore volume. Silica xerogels have about a 0.4 cc/g pore volume. There is, therefore, a 90 percent shrinkage of the silica pores during drying. This huge amount of shrinking is what produces the harder and stronger silica particle and thus the good polishing action.

It has now been found that a silica gel having a 15 to 35 percent by weight water content is a very good dentifrice polishing agent. The effect of the water content on the silica strength is not significant, but using a silica having this water content provides several advantages in a dentifrice formulation. These hydrous silicas yield good clarity to produce a clear gel type dentifrice formulation, provide good polishing and have a higher bulking value, requiring a decreased amount of other components in the formulation. That is, with the pores of the silica gel containing water, the other liquid components which are added to create the particular dentifrice formulation are not adsorbed within the silica pores as when a silica xerogel is used. By not adsorbing other components, these components are preserved. Silica xerogels will adsorb these other components, yielding a wastage of a part of these materials.

It is therefore a prime object of this invention to set out a new class of silicas which can be incorporated into dentifrice compositions and which have very good polishing characteristics. These silicas are silica hydrogels having a water content of 15 to 35 percent by weight.

In brief summary, this invention consists of incorporating hydrous silica gels having an average particle size of from 2 to 30 microns into a dentifrice formulation in a content of 5 to 50 percent by weight of the complete formulation. This hydrous silica gel has a water content of about 15 to 35 percent by weight. These hydrous silica gels exhibit good polishing action and are fully compatible with the other components of the dentifrice formulation.

In more detail, hydrous silica gels are the result of the classical reaction of an alkali silicate with a mineral acid. Sulfuric acid is the most commonly used acid, although other mineral acids such as hydrochloric acid, nitric acid or phosphoric acid can be used. Sodium or potassium silicate may be used as the alkali silicate, with sodium silicate being preferred. The acid is added to the alkali silicate solution until a pH of less than about 5 is reached, with a pH of about 3 to 4.5 being most common. The alkali silicate solution can be mixed during this addition. The resulting product is a solid silica which includes the liquid phase. That is, the silica fully includes the water within its pores. For this reason that the solid phase contains the liquid phase, these silica materials have been termed silica hydrogels, with the dried silica being termed a silica gel. The mode of drying will determine whether the silica gel is a silica aerogel or a silica xerogel. The silica hydrogels after synthesis have a water content of about 60 to 80 percent by weight.

This ability of silica to form these porous polymeric structure may also be termed a precipitation of the silica. On acidulation, silica particles grow and form a solid. This is viewed by some as a precipitation with the fact that all of the liquid phase being contained in the solid phase being fortuitous. However, for the purposes of this application these will be termed hydrogels, since this is a widely accepted term in the silica art.

In producing these silica hydrogels, the alkali silicate solution has an $SiO_2$ concentration of about 6 to 20 percent by weight. A stoichiometric excess of acid is used, thereby reaching the low preferred pH of 3 to 4.5. After the silica hydrogel is formed, it is dried to the water content of 15 to 35 percent by weight (preferably 20 to 30) to yield the hydrous silica gel. This drying can be by oven drying, spray drying, flash drying or some other known method. What is important is that there be remaining an original water content of 15 to 35 percent by weight. This removal of water is an irreversible process. If a silica is dried to essentially complete dryness, it cannot be rehydrated to this same hydrous silica gel. Drying causes irreversible changes in the silica structure. Therefore, in producing these hydrous silica gels useful as polishing agents, the original water content must not be allowed to decrease below about 15 percent by weight. If this occurs, the structure will be substantially shrunk to a dense structure which will not have a high bulking value while being an effective polishing agent.

This silica hydrogel is used in a preferred average particle size range of about 2 to 30 microns. This average particle size range is an average particle size by weight, as determined by Coulter Counter analysis. Average particle size by weight signifies that 50 percent by weight of the particles are above a designated particle size and 50 percent by weight are less than a given particle size. At average particle sizes below about 2 microns, the degree of polishing substantially decreases, although there does remain some polishing action. When the average particle size increases above about 30 microns, and particularly when above about 40 microns, the polishing degrades to an abrasion of the tooth enamel surface. Also, when the average particle size is 40 microns and above, there remains a gritty after-taste in the mouth of the user. This average particle size range of 2 to 30 microns is, therefore, a preferred range, with other sizes also being operable.

Other silicas may be incorporated into the dentifrice formulation to provide additional polishing activity, or to serve as thixotropic agents. Useful additional silicas are silica xerogels, silica aerogels and pyrogenic silicas. These silicas which are to serve as thixotropic agents are preferably in an average particle size range of about 0.5 to 10 microns. An aerogel silica is a silica produced by the acidulation of an alkali silicate solution with an acid followed by the removal of water from the silica pores by a method which minimizes substantial shrinkage of the silica structure. Pyrogenic silicas are those produced by a flame vaporization technique from a silicon halide or an organo-silicon compound. Pyrogenic silicas are available under the trademarks Cabosil and Aerosil, with aerogel silicas being available under the trademarks Santocel and Syloid. If a xerogel silica added is in the particle size range of 2 to 30 microns, this will function mainly as an additional polishing agent.

These additional silica materials are added so as to be in a concentration of about 1 to 20 percent by weight of the total dentifrice formulation. If large quantities of these additional silicas are added, the amount of silica hydrogel which is added can be decreased.

If desired, other polishing agents can be added to the dentifrice formulation. Very useful additional polishing agents are kaolin clays, montmorillonite clays, aluminas, alumino-silicates and zirconium silicate. However, if such a polishing agent is added, the toothpaste formulation will lose the feature of being a clear gel in appearance. Any other standard polishing agent could also be added. The average particle size of any of these additional polishing agents should be in a range of about 2 to 30 microns.

The remaining constituents added to the dentifrice formulation may vary widely. Silica is compatible with just about all other organic and inorganic materials. A fluoride such as stannous fluoride, zirconium fluoride, or sodium fluosilicate can be used. Each of these fluorine compounds contains available fluorine which can be taken up by the enamel of a tooth.

The dentifrice of the invention can also further contain as optional ingredients a soap or synthetic detergent as a surface tension depressant; flavoring materials; buffers; sweeteners such as saccharin; humectants; preservatives and harmless coloring materials, in proportions to give any desired effect. There are conventional components of dentifrices, and materials suitable for this purpose need not be enumerated for they are well known to those skilled in the dentifrice art.

In a preferred embodiment, the dentifrice is in the form of a paste, and in this event it will contain humectant materials and a binder in amounts to give the dentifrice a smooth texture and good flowability. Glycerin and sorbitol are preferred carriers and softeners, but ethyl alcohol, mineral oil, corn syrup, glucose and invert sugars, glycols and honey can also be employed. As binders, there can be used gum tragacanth, sodium carboxymethylcellulose, hydroxyethylcellulose, Indian gum, Irish moss or carragheen and its derivatives, starch, acacia gums, agar-agar, locust bean gum, and pectin. Those skilled in the dentifrice art know other carriers and softeners and binders.

The degree of translucency of the product can be increased or decreased by varying the amount and composition of the humectant materials. For example, certain flavoring materials could be more soluble in one humectant system than in another. Obviously, insoluble flavoring materials will decrease translucency, and appropriate changes in the humectant system to enhance solubility would simultaneously enhance translucency. Additionally, it has been found that greater translucency is obtained when the refractive index of the humectant system is adjusted appropriately. Thus, a system containing appropriate amounts of glycerin, sorbitol and/or water can give a transparent product. The effect can be attributed to a closer matching of the refractive indices of the solid and liquid portions of the dentifrice. An unusual feature of the compositions of the present invention is that a high degree of translucency can be obtained even when the refractive indices are not matched exactly.

The use of the hydrous silica polishing and cleansing ingredient in the dentifrice compositions of the invention permits the incorporation therein of oral health agents such as germicides, antibiotics and astringents. Typical examples thereof include tyrothrycin, chlorophyllins, hexachlorophene, the sarcosides and astringent salts.

Such oral health agents are employed in a beneficial amount normally ranging from about 0.01 percent to about 2 percent by weight of paste dentifrice. The humectants are generally employed in an amount from about 5 percent of about 75 percent by weight of the dentifrice, the binders in an amount from about 0.5 percent to about 30 percent by weight of the dentifrice, flavoring agents in an amount from about 0.1 percent to about 5 percent by weight of the dentifrice, water in an amount from about 4 percent to about 60 percent by weight of the dentifrice, surface tension depressants in an amount from about 0.01 percent to about 6 percent by weight of the dentifrice, and preservatives in an amount from about 0.01 percent to about 2 percent of the dentifrice.

The dentifrices are prepared by blending the components together, with deaeration being necessary for the translucent and transparent toothpastes.

EXAMPLES 1–6

A series of hydrous silica gels were produced by acidulating a sodium silicate solution (12 percent $SiO_2$) with sulfuric acid to a pH of 3.5. This silica hydrogel was washed to remove sodium sulfate and dried to the water content levels as set out in Table I. Table I also sets out the particle size and Radioactive Dentine Abrasion (R.D.A.) test results. Data on Syloid 63 and Syloid 244 is given in this table as a means of comparison to other silicas. Syloid 63 is a silica xerogel and contains about 6.5 percent water by weight. Syloid 244 is an aerogel and is used principally as a thixotropic agent.

Table I

| Example | Percent T.V. | Average Particle Size | Particle Size Range | R.D.A. |
|---|---|---|---|---|
| 1 | 17 | 6.5 | .5–45 | 530 |
| 2 | 24 | 6.2 | .7–37 | 705 |
| 3 | 31 | 10.0 | .7–45 | 482 |
| 4 | 32 | 5.5 | .4–37 | 400 |
| 5 | 5.5 | 2.9 | .5–11 | 71 |
| Syloid 244 | | | | |
| 6 | 6.5 | 6.6 | .4–26 | 608 |
| Syloid 63 | | | | |

The Radioactive Dentine Abrasion Test is as follows:
I. Preparing the Tooth Surface:
The radioactive (about one millicurie by exposing the teeth for 5 hours to a neutron flux of $10^{12}$ neutrons/cm$^2$, the temperature during irradiation not exceeding 40°

C.) specimens of dentine are transferred to the perspex troughs of a standard brushing machine, and their surfaces cleaned of debris, by brushing for 2000 double brush strokes in a slurry of waterworks chalk tooth paste consisting of 20 g tooth paste + 70 g of water.

II. Test:

A slurry of the polishing agent is then added to the troughs (20 g slurry + 10 g water). After ensuring the tooth specimen is adequately covered, it is brushed for 500 strokes. At the end of this run, 15 ml of distilled water are added to the trough, mixed thoroughly with a glass rod, and a further 500 double brush strokes given. This procedure is repeated for a further three additions of 15 ml of distilled water. At the completion of the test the dentine will have been brushed for 2500 double brush strokes.

The active slurry is poured from the trough. After stirring, two 1 ml samples of the slurry are withdrawn with a pipette, and transferred to aluminum planchets 2.5 cm diameter. The slurries are dried under an infrared lamp for one hour.

III. Radiotracer counting:

The radioactivity of the slurry samples is determined with a Geiger micro-counter. To avoid having to make corrections for decay in activity, the counts for all the samples are made within a short period of time. All counts for activity must be corrected for "dead time" and background errors. The order for testing a series of toothpastes is to start and finish with the waterworks chalk reference. This ensures that the wear rate (with respect to the reference) has not altered from the beginning and end of the whole run.

The dentine abrasion value for a particular toothpaste will be the ratio of the corrected counts for that paste to the average count for the reference.

Example 7

| Components | Parts by Weight |
|---|---|
| Hydrous Silica Gel (24% T.V.) | 20.00 |
| Sodium Carboxymethylcellulose | 0.25 |
| Saccharin | 0.20 |
| Sorbitol (70%) | 70.04 |
| Sodium Benzoate | 0.08 |
| Colorant (about 1% solution) | 0.53 |
| Flavor and Chloroform | 1.85 |
| 21% Sodium Lauryl Sulfate - 79% Glycerin MIxture | 7.00 |
| Total | 100 |

The toothpaste was reviewed by a panel for cleansing, taste, grit aftertaste and preference. This toothpaste formulation was ranked to have characteristics similar to a commercial clear toothpaste.

Example 8

| Components | Parts by Weight |
|---|---|
| Hydrous Silica Gel (15* T.V.) | 20.00 |
| Sodium Carboxymethylcellulose | 0.30 |
| Saccharin | 0.20 |
| Glycerine | 24.00 |
| Sorbitol (70%) | 49.99 |
| Sodium lauroyl sarcosinate | 0.08 |
| Colorant (about 1% solution) | 0.53 |
| Flavor and Chloroform | 1.85 |
| 21% Sodium lauryl sulfate (79%) | 3.00 |
| Total | 100 |

The toothpaste was reviewed by a panel for cleansing, taste, grit aftertaste and preference. This toothpaste formulation was ranked to have characteristics similar to a commercial clear toothpaste.

What is claimed is:

1. An oral dentifrice composition providing good polishing of teeth, having as one component a cleansing and polishing agent consisting of a hydrous silica gel containing 17 to 32 percent by weight water, with an average particle size in the range of 2 to 30 microns, said hydrous silica gel comprising from about 5 percent to 50 percent by weight of the oral dentifrice composition and said oral dentifrice composition having a radioactive dentine abrasion value of from 400 to 705.

2. The oral composition as defined by claim 1, which further contains from about 0.01 percent to about 2 percent by weight of an oral health agent selected from the group consisting of tyrothrycin, chlorophyllins, hexachlorophene, the sarcosides, astringent salts, sodium fluoride, lithium fluoride, stannous fluoride, potassium fluoride, ammonium fluoride, sodium fluostannite, stannous chlorofluoride, sodium monofluophosphate and mixtures thereof.

3. A translucent oral composition as defined by claim 1 wherein the hydrous silica gel has an average particle diameter in the range from about 5 to about 25 microns and is present in an amount from about 8 percent to about 20 percent by weight.

4. The translucent oral composition as defined by claim 3 which further contains as a polishing ingredient from about 0.5 percent to about 15 percent by weight of a silica selected from the group consisting of pyrogenic silicas and aerogel silicas.

5. The translucent oral composition as defined by claim 4 which further contains an amount up to about 10 percent by weight of water-insoluble sodium metaphosphate.

6. The oral composition as defined by claim 4 which further contains as a polishing ingredient from about 0.5 percent to about 20 percent by weight of a silica aerogel.

7. A transparent dentifrice composition comprising about 14 percent by weight of a hydrous silica gel containing 17 to 32 percent by weight water and having an average particle diameter of about 10 microns; about 7.5 percent by weight of a porous silica aerogel having an average particle diameter of about 3 microns; about 0.6 percent by weight of sodium carboxymethylcellulose; about 0.2 percent by weight of saccharin; about 47 percent by weight of sorbitol; 2 percent by weight of a flavoring agent; about 7 percent by weight of a 21 percent sodium lauryl sulfate-79 percent glycerin mixture; and about 0.1 percent by weight of a germicide, said transparent dentifrice composition having a radioactive dentine abrasion value of from 400 to 705.

8. A transparent dentifrice composition comprising about 14 percent by weight of a hydrous silica gel containing 17 to 32 percent by weight water and having an average particle diameter of about 10 microns; about 7.5 percent by weight of a silica aerogel having an average particle diameter of about 3 microns; about 0.6 percent by weight of sodium carboxymethylcellulose; about 0.2 percent by weight of saccharin; about 47 percent by weight of sorbitol; about 0.08 percent by weight of sodium benzoate; about 0.5 percent by weight of a 1 percent solution of dye; about 1 percent by weight of a flavoring agent; about 0.8 percent by weight of chloroform; about 7 percent by weight of a sodium lauryl sulfate-glycerin mixture; and the balance substantially water, said transparent dentifrice composition having a radioactive dentine abrasion value of from 400 to 705.

9. A translucent dentifrice composition including a humectant and as a cleansing and polishing agent hydrous silica gel in an amount of 5-50 weight percent of the total composition, said hydrous silica gel containing about 20 to 30 percent by weight water and having a particle size of about 2-30 microns, said translucent dentifrice composition having a radioactive dentine abrasion value of from 400 to 705.

* * * * *